(12) United States Patent
Carapezza et al.

(10) Patent No.: US 12,064,589 B2
(45) Date of Patent: Aug. 20, 2024

(54) APPARATUS, SYSTEM AND METHOD FOR HEATING FLUIDS

(71) Applicant: JABIL INC., St. Petersburg, FL (US)

(72) Inventors: William Carapezza, St. Petersburg, FL (US); Rodney Medley, St. Petersburg, FL (US)

(73) Assignee: JABIL INC, St. Petersburg, FL (US)

(*) Notice: Subject to any disclaimer, the term of this patent is extended or adjusted under 35 U.S.C. 154(b) by 569 days.

(21) Appl. No.: 17/116,904

(22) Filed: Dec. 9, 2020

(65) Prior Publication Data
US 2021/0162116 A1  Jun. 3, 2021

Related U.S. Application Data

(63) Continuation of application No. 15/548,379, filed as application No. PCT/US2016/016843 on Feb. 5, 2015, now abandoned.
(Continued)

(51) Int. Cl.
*A61M 5/14* (2006.01)
*A61M 5/142* (2006.01)
(Continued)

(52) U.S. Cl.
CPC .......... *A61M 5/1407* (2013.01); *A61M 5/142* (2013.01); *A61M 5/168* (2013.01);
(Continued)

(58) Field of Classification Search
CPC ...... B01F 33/84; B01F 35/93; B01F 2035/99; B01F 2101/21; B29C 45/74; C12M 41/24; A61M 5/1407
See application file for complete search history.

(56) References Cited

U.S. PATENT DOCUMENTS

| | | | | |
|---|---|---|---|---|
| 2,939,770 A | * | 6/1960 | Fritz | B01J 19/20 366/168.1 |
| 5,101,804 A | * | 4/1992 | Cohn | F24V 30/00 604/113 |

(Continued)

FOREIGN PATENT DOCUMENTS

EP  2471377 A1  7/2012

OTHER PUBLICATIONS

International Search Report for PCT/US2016/016843, dated May 17, 2016.
(Continued)

*Primary Examiner* — Elizabeth Insler
(74) *Attorney, Agent, or Firm* — Riverside Law LLP

(57) ABSTRACT

Apparatus, system and method for heating fluid from a plurality of fluid sources. A heating chamber top portion includes a plurality of fluid inlet tubes configured to pass fluid from the plurality of fluid sources. A heating chamber may be coupled to the heating chamber top portion, the heating chamber collectively receives at least some of the fluid from the plurality of fluid sources. At least one heating element configured within the heating chamber heats the received fluid from the plurality of fluid sources. An agitator mixes the received fluid from the plurality of fluid sources in the heating chamber, wherein the agitator is configured to mix the received fluid from the plurality of fluid sources by rotationally turning within the heating chamber.

10 Claims, 5 Drawing Sheets

Related U.S. Application Data

(60) Provisional application No. 62/112,526, filed on Feb. 5, 2015.

(51) Int. Cl.
| | |
|---|---|
| *A61M 5/168* | (2006.01) |
| *A61M 5/172* | (2006.01) |
| *A61M 5/44* | (2006.01) |
| *B01F 3/08* | (2006.01) |
| *B01F 7/00* | (2006.01) |
| *B01F 7/08* | (2006.01) |
| *B01F 15/00* | (2006.01) |
| *B01F 15/06* | (2006.01) |
| *B01F 23/43* | (2022.01) |
| *B01F 27/114* | (2022.01) |
| *B01F 27/72* | (2022.01) |
| *B01F 35/21* | (2022.01) |
| *B01F 35/221* | (2022.01) |
| *B01F 35/93* | (2022.01) |
| *B01F 35/90* | (2022.01) |
| *B01F 101/00* | (2022.01) |

(52) U.S. Cl.
CPC ............. *A61M 5/172* (2013.01); *A61M 5/44* (2013.01); *B01F 23/43* (2022.01); *B01F 27/1141* (2022.01); *B01F 27/72* (2022.01); *B01F 35/2115* (2022.01); *B01F 35/2215* (2022.01); *B01F 35/93* (2022.01); *A61M 2205/3306* (2013.01); *A61M 2205/3368* (2013.01); *A61M 2205/36* (2013.01); *A61M 2205/50* (2013.01); *A61M 2205/587* (2013.01); *A61M 2205/75* (2013.01); *B01F 2035/99* (2022.01); *B01F 2101/2202* (2022.01)

(56) References Cited

U.S. PATENT DOCUMENTS

| | | | |
|---|---|---|---|
| 5,108,372 A | | 4/1992 | Swenson |
| 5,698,163 A | * | 12/1997 | Mandel ................. G05D 21/02 |
| | | | 422/111 |
| 6,627,174 B1 | * | 9/2003 | Judat ..................... B01J 19/006 |
| | | | 406/197 |
| 7,459,258 B2 | * | 12/2008 | Chung ................ G03G 9/0806 |
| | | | 430/137.14 |
| 2006/0178619 A1 | | 8/2006 | Simpkins |
| 2010/0221568 A1 | * | 9/2010 | Kruse ..................... B01F 35/92 |
| | | | 366/342 |
| 2011/0184501 A1 | | 7/2011 | Gill et al. |
| 2012/0241045 A1 | * | 9/2012 | Aouad ................. B01F 35/832 |
| | | | 141/83 |

OTHER PUBLICATIONS

Written Opinion of the International Searching Authority for PCT/US2016/016843, dated May 2, 2016.
International Preliminary Report on Patentability for PCT/US2016/016843, dated Aug. 8, 2017.

\* cited by examiner

APPARATUS, SYSTEM AND METHOD FOR HEATING FLUIDS

CROSS-REFERENCE TO RELATED APPLICATIONS

The present disclosure is a Continuation Application of U.S. application Ser. No. 15/548,379, entitled: APPARATUS, SYSTEM AND METHOD FOR HEATING FLUIDS, filed Aug. 2, 2017; which claims priority to International Application No. PCT/US2016/016843, entitled: "APPARATUS, SYSTEM AND METHOD FOR HEATING FLUIDS," filed Feb. 5, 2016, which claims priority to U.S. Provisional Application No. 62/112,526, entitled "APPARATUS, SYSTEM AND METHOD FOR CONNECTING TO, MONITORING AND CONTROLLING BODILY WASTE RECEPTACLES," filed Feb. 5, 2015, the contents of which is incorporated by reference in its entirety herein.

FIELD OF THE DISCLOSURE

The present disclosure is directed to an apparatus, system and method for heating fluid, such as intravenously (IV) delivered fluids. More specifically, the present disclosure is directed to receiving multiple fluid sources, such as multiple intravenous (IV) fluids, and heating them collectively in a heating chamber.

BACKGROUND

Many emergency department (ED) patients in the United States are treated with intravenous (IV) fluids. These fluids are typically stored at room temperature and infused into patients without heating. During infusion of room temperature IV fluids, some patients experience shivering, chills and discomfort due to hypothermic effects of the non-heated fluid. Recently, heating devices have been developed for heating IV fluids to body temperature (normothermia) prior to infusion, such as to reduce shivering and improve patient comfort in the perioperative period.

Conventional fluid warmers rely on techniques such as dry heat, countercurrent water bath heating, convective air heating, countercurrent metal heating and in-line microwave heating for heating fluids. While such techniques are suitable for simple fluid heating applications, they are not particularly effective at handling and heating multiple IV fluid sources. Preparation of IV fluids can be complicated, because they may be isotonic, and may combine drugs, nutrients, and/or electrolytes at specific concentrations. Often a needed solution or a series of solutions of known concentrations are first produced by first preparing a single stock solution. Aliquots (predetermined measured volumes) of the stock solution can then be diluted to desired volumes and/or concentrations. However, in many cases, it can be inconvenient to accurately prepare a needed volume of a dilute solution. But, as noted above, conventional fluid warmers have not been effective in mixing IV fluid from multiple sources during the heating process, thus necessitating accurate preparation of a dilute solution in order enable use of such conventional fluid warmers.

Therefore, the need exists for improved embodiments of IV fluid warmers.

BRIEF SUMMARY

Accordingly and in illustrative embodiments, an apparatus and system is disclosed for heating fluid from a plurality of fluid sources, comprising a heating chamber top portion comprising a plurality of fluid inlet tubes configured to pass fluid from the plurality of fluid sources; a heating chamber coupled to the heating chamber top portion, the heating chamber configured to collectively receive at least some of the fluid from the plurality of fluid sources; at least one heating element configured within the heating chamber for heating the received fluid from the plurality of fluid sources; and an agitator for mixing the received fluid from the plurality of fluid sources in the heating chamber, wherein the agitator is configured to mix the received fluid from the plurality of fluid sources by rotationally turning within the heating chamber. In one non-limiting example, the agitator comprises a helical-shaped agitator for mixing the received fluid from the plurality of fluid sources.

In additional illustrative embodiments, a method is disclosed for heating fluid from a plurality of fluid sources, comprising passing fluid from the plurality of fluid sources to a heating chamber top portion comprising a plurality of fluid inlet tubes; collectively receiving at least some of the fluid from the plurality of fluid sources in a heating chamber coupled to the heating chamber top portion; heating the received fluid from the plurality of fluid sources via at least one heating element within the heating chamber; and mixing, by an agitator, the received fluid from the plurality of fluid sources in the heating chamber, wherein the agitator mixes the received fluid from the plurality of fluid sources by rotationally turning within the heating chamber.

Thus, the disclosed embodiments provide improved embodiments of IV fluid warmers. These embodiments may provide functional improvement over the known art, may be smaller and lighter than the known art, and may provide other advantageous features that will be made more apparent from the Detailed Description, below.

BRIEF DESCRIPTION OF THE FIGURES

The present invention is illustrated by way of example and not limitation in the figures of the accompanying drawings, in which like references indicate similar elements and in which.

DETAILED DESCRIPTION

Figure 1:
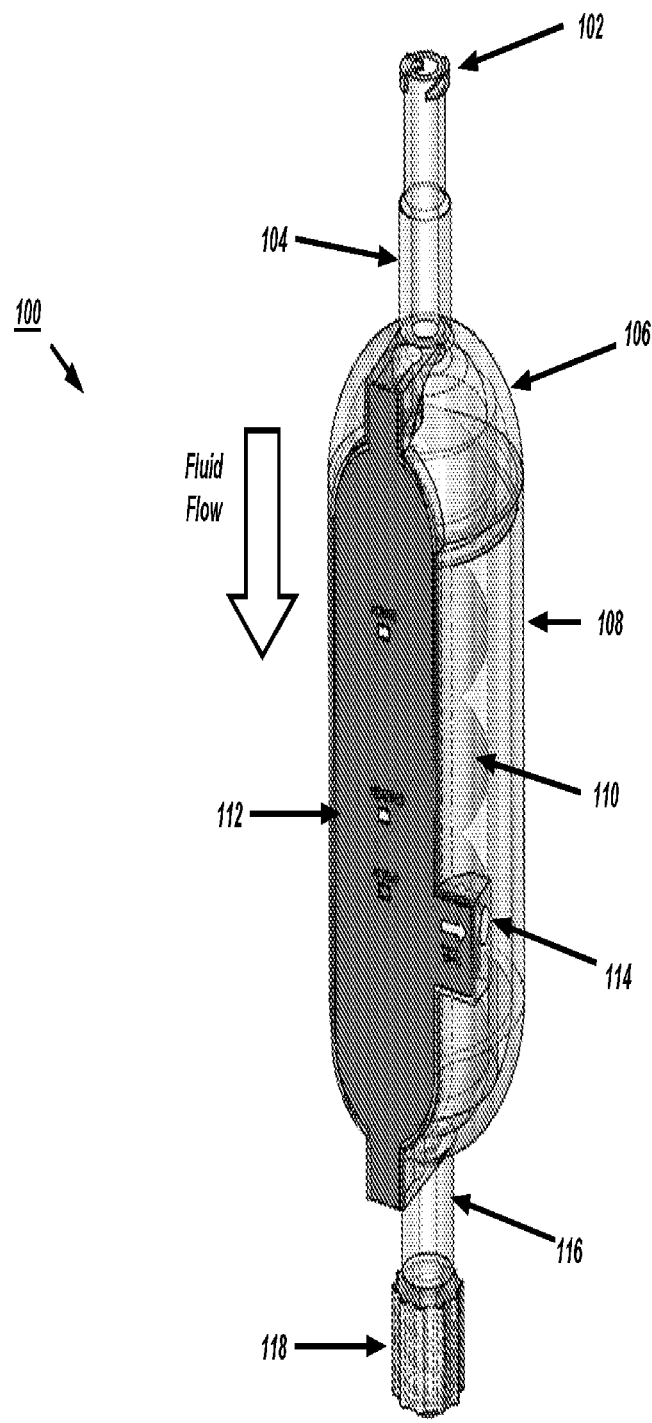
FIG. 1 shows an illustrative embodiment of a fluid heating chamber body assembly comprising an inlet tube and outlet tube and a helical heating element.

It is to be understood that the figures and descriptions of the present disclosure have been simplified to illustrate elements that are relevant for a clear understanding of the embodiments, while eliminating, for the purpose of clarity, many other elements found in known apparatuses, systems, and methods. Those of ordinary skill in the art may thus recognize that other elements and/or steps are desirable and/or required in implementing the disclosure. However, because such elements and steps are known in the art, and because they consequently do not facilitate a better understanding of the disclosure, for the sake of brevity a discussion of such elements and steps is not provided herein. Nevertheless, the disclosure herein is directed to all such elements and steps, including all variations and modifications to the disclosed elements and methods, known to those skilled in the art. Exemplary embodiments will now be described more fully with reference to the accompanying drawings.

Exemplary embodiments are provided so that this disclosure will be thorough, and will fully convey the scope to those who are skilled in the art. Numerous specific details are set forth, such as examples of specific components, devices, and methods, to enable a thorough understanding of embodiments of the present disclosure. It will be apparent to those skilled in the art that specific details need not be employed, that is, that the exemplary embodiments may be embodied in many different forms and thus should not be construed to limit the scope of the disclosure. For example, in some exemplary embodiments, well-known processes, well-known device structures, and well-known technologies are not described in detail.

The terminology used herein is for the purpose of describing particular example embodiments only and is thus not intended to be limiting. As used herein, the singular forms "a", "an" and "the" may be intended to include the plural forms as well, unless the context clearly indicates otherwise. The terms "comprises," "comprising," "including," and "having," are inclusive and therefore specify the presence of stated features, integers, steps, operations, elements, and/or components, but do not preclude the presence or addition of one or more other features, integers, steps, operations, elements, components, and/or groups thereof. The method steps, processes, and operations described herein are not to be construed as necessarily requiring their performance in the particular order discussed or illustrated, unless specifically identified as having an order of performance. It is also to be understood that additional or alternative steps may be employed.

When an element or layer is referred to as being "on", "engaged to", "connected to," "coupled to," or a like term or phrase with respect to another element or layer, it may be directly on, engaged, connected or coupled to the other element or layer, or intervening elements or layers may be present. In contrast, when an element is referred to as being "directly on," "directly engaged to", "directly connected to" or "directly coupled to" another element or layer, there may be no intervening elements or layers present. Other words used to describe the relationship between elements should be interpreted in a like fashion (e.g., "between" versus "directly between," "adjacent" versus "directly adjacent," etc.). As used herein, the term "and/or" includes any and all combinations of one or more of the associated listed items.

Although the terms first, second, third, etc. may be used herein to describe various elements, components, regions, layers and/or sections, these elements, components, regions, layers and/or sections should not be limited by these terms. These terms may be only used to distinguish one element, component, region, layer or section from another element, component, region, layer or section. Terms such as "first," "second," and other numerical terms when used herein do not imply a sequence or order unless clearly indicated by the context. Thus, a first element, component, region, layer or section discussed below could be termed a second element, component, region, layer or section without departing from the teachings of the exemplary embodiments.

The various exemplary embodiments will be described herein below with reference to the accompanying drawings. In the following description and the drawings, well-known functions or constructions are not shown or described in detail since they may obscure the invention in unnecessary detail.

Turning now to FIG. 1, illustrated is a fluid heating chamber body assembly 100 comprising an inlet tube 102 and inlet tube body 104 for receiving one or more sources of fluid for heating (shown in the direction of the arrow in FIG. 1). This and other disclosed embodiments herein for heating fluid may be advantageously deployed in medical or laboratory settings, by way of non-limiting example. In the non-limiting example of FIG. 1, inlet tube 102 may be configured with a receiving portion (female connector portion) that allows connectors or couplers, such as a luer cap or other suitable connector, to releasably couple to the inlet tube 102. Of course, those skilled in the art can appreciate that other configurations for receiving portion 102 are contemplated in the present disclosure. For example, inlet tube 102 may be configured with a connector or coupler that connects with a receiving end of a tube, container and/or device.

In certain embodiments, inlet tube body 104 may be integrated as part of a heating chamber top portion 106, which may be coupled to heating chamber body 108. Heating chamber top portion 106 may be integrated together with heating chamber body 108, or may be releasably coupled thereto. In certain embodiments, heating chamber body 108 may enclose one or more heating elements (see 208A-208B, FIG. 2) that serve as, or are coupled to, an agitator 110. Temperature reading and/or control may be provided by circuitry on heating chamber body 108 and readings/inputs may be provided on face plate 112, which may include one or more LEDs, screens, controls, buttons, switches or the like. Agitator 110 is shown here as a helical-shaped (or "auger-like") agitator that may serve to agitate fluids, and particularly multiple fluid sources, entering the heating chamber body 108. Agitator 110 may be manufactured from any rigid or semi-rigid plastic, metal, or any other suitable material.

In this non-limiting example, agitator 110 is shown as a solid-body component. This configuration may advantageously serve to mix multiple fluid sources from the inlet tube body 108 before they are received in the outlet tube body 116, which may connect to a patient or external device via a tube configured to connect with coupler 118. The agitator 110 may be configured to rotationally turn within heating chamber body 108 from the force of the fluid(s) being pumped into or otherwise entering heating chamber body 108. In embodiments, the agitator 110 may rotate or be stationary, and may itself serve, at least in part, as a heating element to heat fluid(s) in chamber body 108.

In one non-limiting example, agitator 110 may be configured to be coupled to a motor (see FIG. 5), or a solenoid, piezo mechanism, etc., within the heating chamber body 108 to assist in rotation. Such a configuration may be advantageous in instances wherein incoming fluid flow from inlet tube body 104 is at a lower or reduced rate. In another non-limiting example, the motor may controlled by a controller, such as a processor or microcontroller (see 226, FIG. 2) to ensure that the flow or pressure of the fluid to outlet tube body 116 remains constant and/or does not exceed a predetermined amount.

While agitator 110 is shown in the non-limiting example as a solid-body component, it should be understood by those skilled in the art that other configurations are contemplated in the present disclosure as well. For example, at least a portion of the surface of agitator 110 may be perforated to allow fluid to more freely mix laterally within heating chamber body 108. Such perforations may be of any suitable size, shape, and/or pattern to allow greater lateral fluid flow within heating chamber body 108. In another non-limiting example, multiple slits may be provided across and/or along the agitator 110 surface to achieve a similar effect. In a further non-limiting example, at least a portion of the agitator 110 surface may be configured as a mesh. By providing additional lateral fluid flow capability within heating chamber body 108, greater lateral fluid flow may be achieved to enhance mixing, while excessive fluid pressure buildup resulting from the agitator 110 rotation in the heating chamber body may be reduced or minimized.

As mentioned previously, the helical shape of agitator 110 may provide an efficient mechanism for mixing fluids within heating chamber body 108. However, one skilled in the art should recognize that other agitator 110 shape configurations are also contemplated by the present disclosure. In one non-limiting example, agitator 110 may be configured with a central cylindrical or polyhedron-shaped core extending generally from inlet tube body 104 to outlet tube body 116. The core may be configured with extenders, such as fins, flaps, or panels of a generally planar shape extending perpendicularly from the core. In a non-limiting example, the extenders may be angled and/or offset obliquely from the surface of the core to provide a specific agitation effect from the rotation of the core within heating chamber. In a non-limiting example, instead of being a generally planar shape, the extenders may be cupped, twisted and/or bent along an axis extending from the core surface (e.g., propeller-shaped) to achieve a particular hydrodynamic agitation effect within heating chamber body 108. In certain embodiments, agitator 110 may be a static mixing baffle. Various agitator 110 configurations may be advantageous for mixing fluids having particular fluid densities and/or compositions that may be found in medical and/or industrial applications.

Figure 2:
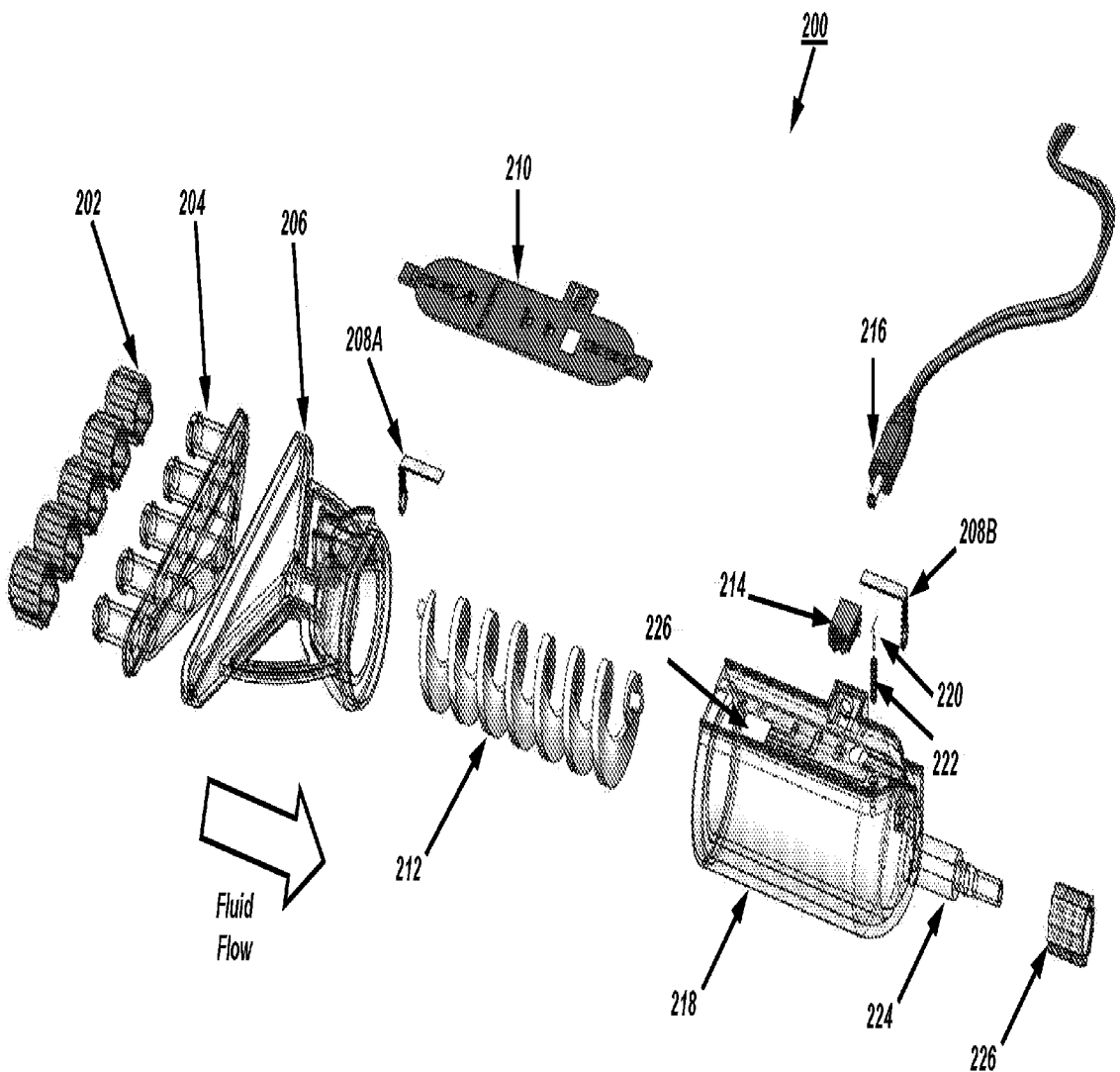
FIG. 2 shows an exploded view of an illustrative embodiment of the heating body assembly of FIG. 1 operatively coupled to a heating chamber top comprising a connector array for receiving a plurality of fluid sources.

Turning now to FIG. 2, a multiple-fluid-source heating chamber body assembly 200 is shown in an illustrative embodiment, wherein the heating chamber top portion 206 includes a multiple inlet tube assembly 204 with associated couplers 202 for receiving a plurality of fluid sources configured to flow in the direction of the arrow show in FIG. 2. Heating chamber top portion 206 may be releasably coupled to heating chamber body 218. One or more ports 204 may serve as an injection port for assembly 200, and/or those skilled in the art will appreciate, in light of the disclosure, that one or more additional injection ports may be included to provide fluid(s) (e.g., IV fluids) for mixing with other incoming fluids (e.g., IV fluids), either prior to or following pass-through of fluids through heating chamber 218. As in the example of FIG. 1, heating chamber top portion 206 may also be integrated with heating chamber body 218.

Heating element contacts 208A-208B may be positioned at distal ends of heating chamber body 218 to provide heat to the interior of heating chamber body 218, while agitator 212 may perform similarly to agitator 110 discussed above in connection with the example in FIG. 1. In certain non-limiting embodiments, a single heating contact may be used within heating chamber body 218. In other non-limiting embodiments, two (208A-208B) or more heating contacts may be used. The contacts may be positioned within any suitable area of heating chamber body 218, and should be positioned such as so that they do not interfere with or impede agitator 110. As mentioned above, the agitator 110 may also be configured as a separate heating element as well.

Heating chamber body 210 may further include circuitry 226 to control heating element contacts 208A-208B and/or process feedback data from one or more sensors, such as thermistor 220, which may be encased in a thermistor bulb or probe 222 that extends into heating chamber body 210. In certain illustrative embodiments, optical sensing may be utilized as well. A more detailed discussion of the thermistor and heating contact assembly is provided below in connection with FIG. 4.

Circuitry 226 may include a processing apparatus including a processor, memory and other suitable circuitry for providing control and/or data signals via electrical and/or data lines, including networked data lines. In one non-limiting example, circuitry may include a motor controller for controlling rotation of agitator 212. In a non-limiting example, circuitry 226 may provide communications via any suitable wired communication protocol, including, but not limited to, RS-232, SMBus, I2C, USB, IEEE-1394 and the like. The communications circuitry may also provide wireless communications to communicate with external devices via any suitable wireless protocol including, but not limited to, WiFi, Bluetooth, or any other suitable wireless protocol known in the art. As discussed above in connection with FIG. 1, inputs to circuitry 226 may be provided via buttons, touch pads, or other suitable mechanisms via face plate 210. Furthermore, heating chamber characteristic data (e.g., temperature, flow, pressure, etc.) may be processed by circuitry 226 and displayed on a display of face plate 210 and/or communicated externally. As further illustrated in the embodiment of FIG. 3, the temperature may be provided on the display of face plate 210, either as a separate digital readout, such as the illustrated LED digital readout of FIG. 3, distinct from the LED/screen status display(s) discussed herein, or in conjunction with the status, etc., on the LED/screen status displays discussed herein.

In certain embodiments, power for circuitry 226 may be provided by a power source (e.g., 12 VDC converted AC power) via power cord 216 when coupled to power jack 214. In certain embodiments, power may be provided by a battery or battery pack. Heated and mixed fluid may be directed to outlet tube body 224 to a recipient destination (e.g., patient, secondary device). Outlet tube body 224 may couple to additional tubing via coupler 226.

Figure 3:
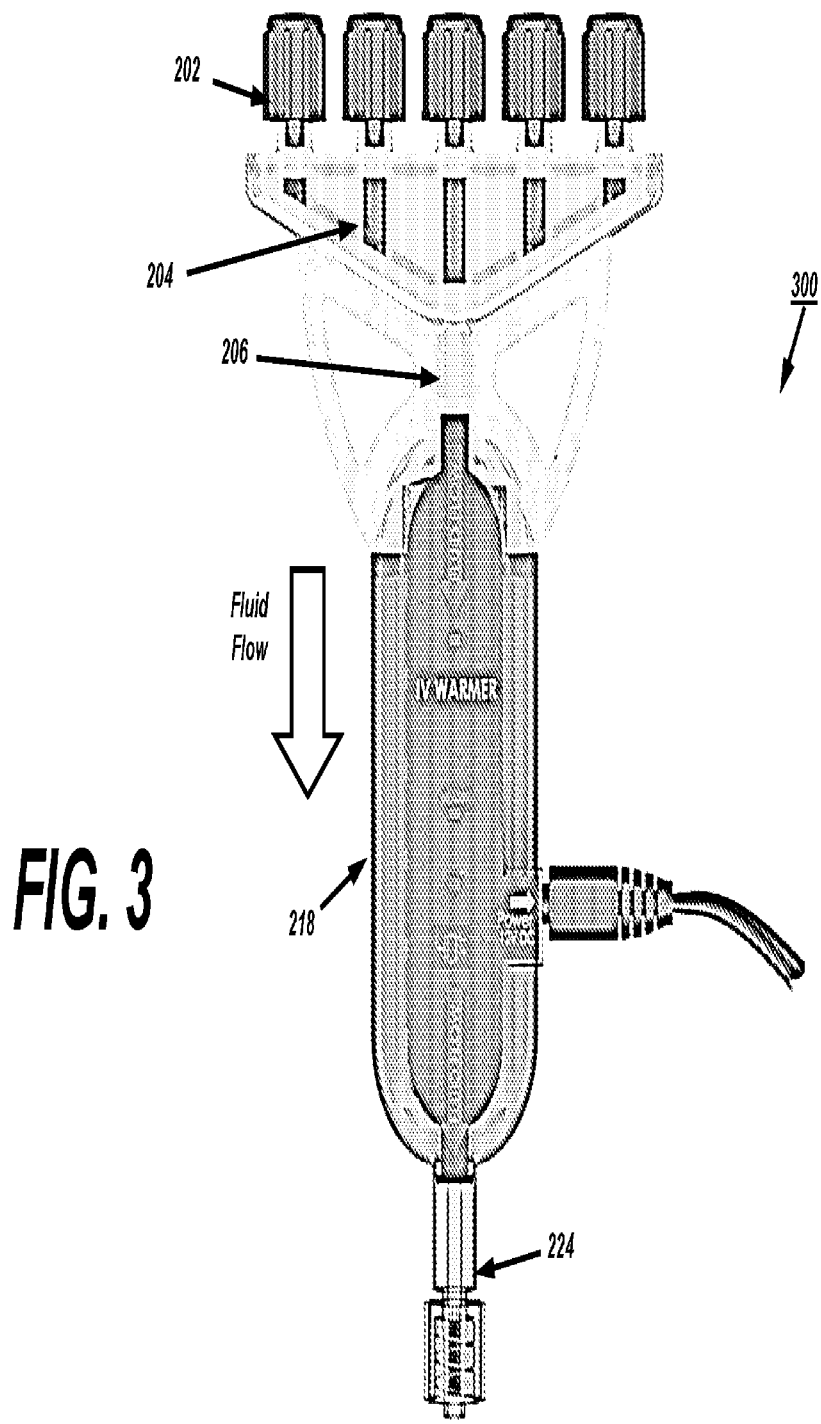
FIG. 3 shows a front view of the fluid heating assembly of FIG. 2 under an illustrative embodiment.

An embodiment of an assembled multiple-fluid-source heating chamber body assembly 300 is shown in FIG. 3. Multiple fluid source lines may be coupled to assembly 300 via couplers 202, where they flow in the direction of the arrow through each respective inlet tube 204 and collectively through inlet tube 206 to heating chamber body 218, which heats and mixes the fluids in any manner described herein and forces the heated/mixed fluids through outlet tube 224. In the illustrated example, a current temperature may be displayed via LED readout.

Figure 4:
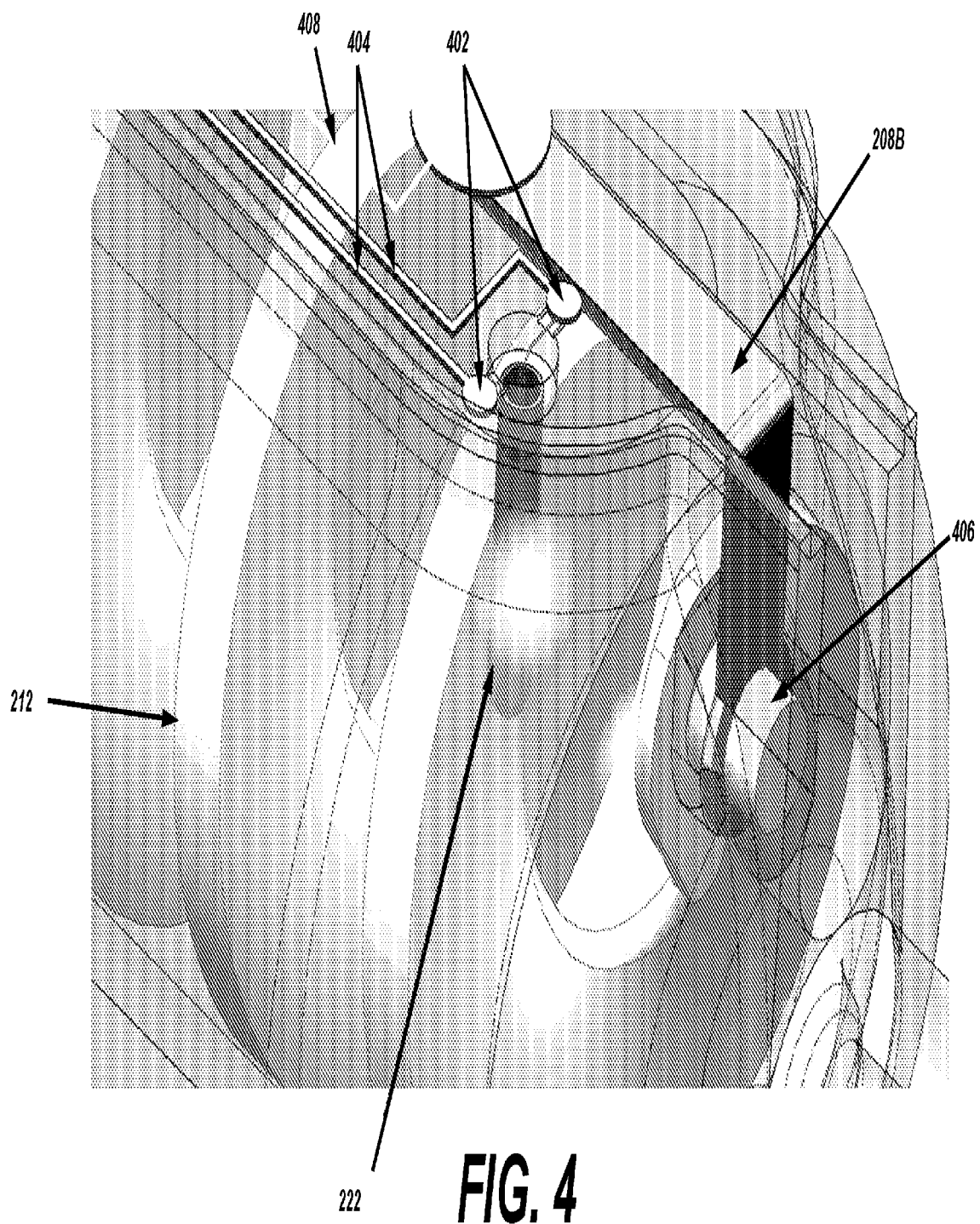
FIG. 4 shows a magnified cutaway perspective view of a front portion of the fluid heating chamber body comprising a thermistor probe under an illustrative embodiment.

Turning now to FIG. 4, a non-limiting example is shown illustrating a configuration for a thermistor assembly 222 comprising a temperature probe (220) positioned within a respective tube 222. In certain embodiments, tube 222 may be manufactured from stainless steel that is press fit into the housing (218). In certain embodiments, tube 222 may be manufactured from other suitable materials such as metals or plastics. In certain embodiments, the temperature probe may be a thermistor or a resistance temperature detector (RTD). Assuming, as a first order approximation that the relationship between resistance and temperature is linear, then temperature may be determined by a change in resistance (ΔR) that is determined by ΔR=kΔT, where ΔT is a change in temperature and k is the temperature coefficient of resistance. k may be set to positive so that the resistance increases with increasing temperature (positive temperature coefficient thermistor, or posistor), or k may be set to negative so that the resistance decreases with increasing temperature, (negative temperature coefficient thermistor). In certain embodiments, thermistor may be configured using third-order approximation of temperature sensing using a Steinhart-Hart approach, which may be expressed by $$\frac{1}{T} = A + Bln(R) + C(\ln(R))^3,$$

where T is the temperature, R is the resistance at T, and A, B, C are Steinhart-Hart coefficients, which vary depending on the type and model of thermistor and the temperature range of interest. Of course, other suitable temperature sensors and techniques, such as silicon bandgap temperature sensors, may be used.

Thermistor assembly 222 may be coupled to contact pads 402, which may be configured to run electrical and/or data signals to and from thermistor assembly 222 using signal lines 404. Control signals and data may be transmitted by circuitry 226 to thermistor assembly 222 via signal lines 404. Similarly, temperature readings and related data from thermistor assembly 222 may be transmitted to circuitry 226 via signal lines 404. An illustrative configuration for heating element contact 208B is shown in FIG. 4, where signal line 408 provides power for heating contact 208B.

Figure 5:
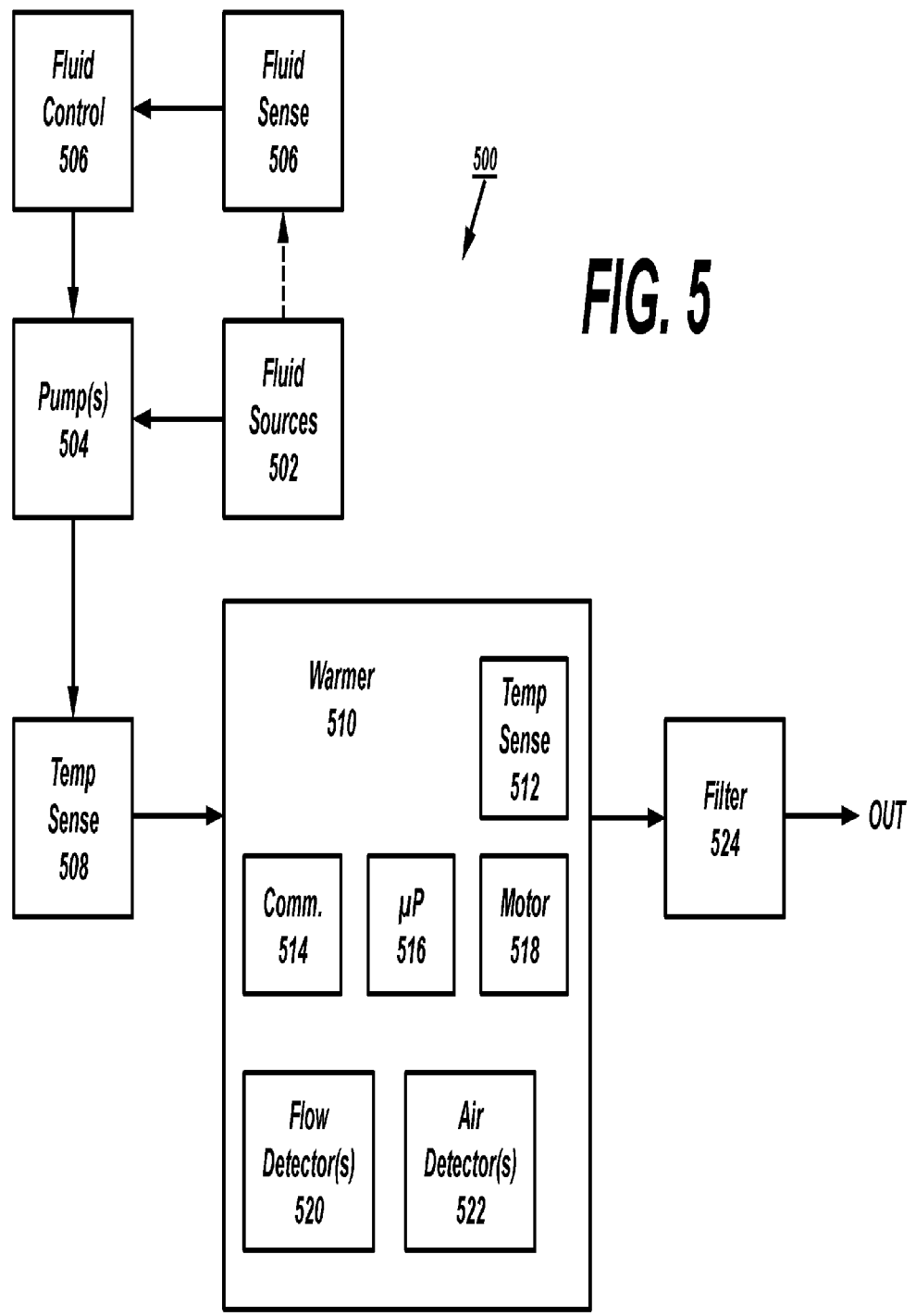
FIG. 5 shows a system for sensing and controlling multiple fluid sources coupled to a fluid heating assembly under an illustrative embodiment.

Turning now to FIG. 5, an embodiment for a fluid heating system 500 is shown. In certain embodiments, multiple fluid sources 502 may be supported or provided, which may include IV bags or other fluid containers. One or more fluid sensors 506 may be provided for determining fluid amounts/weights. In certain embodiments, fluid sensors 506 may include a point level liquid detector, such as magnetic and/or mechanical float, pneumatic, or conductive sensors. In certain embodiments, fluid sensors 506 may include sensors for both point level detection or continuous monitoring, such as ultrasonic, capacitive, optical and/or microwave sensors. In certain embodiments, sensors 506 may include continuous level measurement sensors, such as magnetostrictive, resistive chain, magnetoresistive, hydrostatic pressure, air bubbler and gamma ray sensors.

Fluid sensors 506 may communicate with fluid control module 506, which in turn may control the flow of fluid sources 502 via pumps 504 based at least in part on the signals provided from fluid sensors 506. In certain embodiments, one or more external temperature sensors 508 may be provided to determine an incoming temperature of one or more fluid lines entering fluid warmer 510, which may be configured as the warmer described above in connection with FIGS. 2-3. Such a configuration may be used to determine temperature deltas (i.e., difference between incoming fluid temperature versus required fluid temperature) and for determining levels of preheating in warmer 510 that may be required. For example, an external temperature sensor 508 may sense that one or more incoming fluids are in a cooled (e.g., refrigerated) state. By communicating (e.g., via communications 514) the cooled temperature measurement to processor 516, the warmer 510 may initially increase a heating temperature of any of heating elements (208A-208B; 212) to compensate for the incoming cooled fluid. Similarly, if external temperature sensor 508 senses that one or more incoming fluids are already in a warmed state, the warmer 510 may minimize the heating temperature of any of the heating elements.

Fluid warmer 510 receives the plurality of incoming fluid sources from 502, wherein an agitator and heating element(s) mix and heat the fluids. In certain embodiments, a fluid warmer temperature sensor 512 (e.g., thermistor 220) senses the internal chamber temperature of warmer and may communicate with processor 516 to monitor, control and/or adjust heating levels. Fluid warmer 510 may also receive data and/or control signals via communications 514 (which, for example, may be a part of circuitry 226) for maintaining a desired temperature, activating/deactivating heating elements, controlling heating elements and/or controlling rotation and/or heating of agitator 212.

In certain embodiments, warmer 510 may also include a flow detector 520 and/or air detector 522. Flow detector 520 may be configured to detect incoming and/or outgoing flow rates to ensure that proper fluid pressure is provided at an outlet tube of warmer 510. As mentioned above, a motor 518 may be provided to control rotation of an agitator and thereby affect outgoing fluid flow. Air detector 522 may be configured to sense the existence of air bubbles within the fluid chamber of warmer 510. In certain embodiments, air detector 522 may be configured to provide a warning signal to processor 516 to indicate the presence of air, which may be harmful to a patient when warmer 510 is utilized for medical purposes. The air detector 522 warning signal may include a control signal to activate a valve or clamp (not shown) to shut off fluid flow. When warmer 510 is utilized for medical applications, it may be advantageous to provide one or more filters 524 to filter outgoing fluid and remove any potential impurities and/or solids that may have been present within the fluid mixture.

Those of skill in the art will appreciate that the herein described systems and methods may be subject to various modifications and alternative constructions. There is no intention to limit the scope of the invention to the specific constructions described herein. Rather, the herein described systems and methods are intended to cover all modifications, alternative constructions, and equivalents falling within the scope and spirit of the invention and its equivalents.

Moreover, it can be seen that various features may be grouped together in a single embodiment during the course of discussion for the purpose of streamlining the disclosure. This method of disclosure is not to be interpreted as reflecting an intention that any claimed embodiments require more features than are expressly recited in each claim.

What is claimed is:

1. A method for heating fluid from a plurality of fluid sources to generate a combined solution for intravenous delivery to a patient, comprising:
   passing fluid from the plurality of fluid sources to a heating chamber top portion comprising a plurality of fluid inlet tubes;
   collectively receiving at least some of the fluid from the plurality of fluid sources in a heating chamber coupled to the heating chamber top portion;
   heating the received fluid from the plurality of fluid sources to an approximate body temperature of the patient via at least one heating element within the heating chamber;
   mixing, by an agitator, the received fluid from the plurality of fluid sources in the heating chamber into the combined solution, wherein the agitator mixes the received fluid from the plurality of fluid sources by rotationally turning; and passing the heated combined solution to an outlet tube.

2. The method of claim 1, wherein, for the mixing, the agitator comprises a helical-shaped agitator for mixing the received fluid from the plurality of fluid sources.

3. The method of claim 2, wherein, for the mixing, at least a portion of the agitator comprises a perforated surface.

4. The method of claim 1, further comprising determining, by a temperature sensor, a temperature of the received fluid from the plurality of fluid sources within the heating chamber.

5. The method of claim 4, further comprising providing a control signal by a processor coupled to the temperature sensor, to modify heating power for the at least one heating element based on the determined temperature.

6. The method of claim 4, further comprising displaying the temperature determined by the temperature sensor.

7. The method of claim 4, further comprising transmitting the determined temperature by communications coupled to the temperature sensor.

8. The method of claim 1, further comprising providing, by a motor, rotational force for the agitator to turn within the heating chamber for mixing the received fluid from the plurality of fluid sources.

9. The method of claim 7, further comprising providing, by a processor coupled to the motor, a signal to modify the rotational force provided by the motor.

10. The method of claim 1, further comprising pumping fluid by one or more pumps from the plurality of fluid sources to the fluid inlet tubes.

\* \* \* \* \*